US012672911B2

(12) United States Patent　　(10) Patent No.:　US 12,672,911 B2

Horn et al.　　(45) Date of Patent:　Jul. 7, 2026

(54) RESECTOSCOPE AND ELECTRODE INSTRUMENT FOR A RESECTOSCOPE

(71) Applicant: OLYMPUS WINTER & IBE GMBH, Hamburg (DE)

(72) Inventors: Martin Horn, Hamburg (DE); Christian Brockmann, Hollenstedt (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 468 days.

(21) Appl. No.: 18/132,106

(22) Filed: Apr. 7, 2023

(65) Prior Publication Data

US 2024/0008918 A1　　Jan. 11, 2024

Related U.S. Application Data

(60) Provisional application No. 63/359,917, filed on Jul. 11, 2022.

(51) Int. Cl.
　　*A61B 18/14*　　(2006.01)
　　*A61B 17/00*　　(2006.01)
　　*A61B 18/00*　　(2006.01)

(52) U.S. Cl.
　　CPC .. *A61B 18/149* (2013.01); *A61B 2017/00738* (2013.01); *A61B 2018/00601* (2013.01); *A61B 2018/1475* (2013.01)

(58) Field of Classification Search
　　CPC ....... A61B 18/149; A61B 18/12; A61B 18/14; A61B 2018/00601; A61B 2018/1475; A61B 2018/00982; A61B 2018/144; A61B 2018/1405; A61B 2018/1412; A61B 2017/00738; A61B 17/320016
　　See application file for complete search history.

(56) References Cited

U.S. PATENT DOCUMENTS

| | | | |
|---|---|---|---|
| 7,731,655 B2 | 6/2010 | Smith et al. | |
| 2004/0242959 A1* | 12/2004 | Nosel | A61B 18/149 |
| | | | 600/105 |
| 2019/0053692 A1* | 2/2019 | Stühle | A61B 18/149 |
| 2020/0289189 A1* | 9/2020 | Brockmann | A61B 18/149 |
| 2021/0186595 A1 | 6/2021 | Brockmann et al. | |

FOREIGN PATENT DOCUMENTS

| | | |
|---|---|---|
| DE | 10 2018 127 919 A1 | 5/2020 |
| JP | S61-180001 U | 11/1986 |
| JP | H11-511674 A | 10/1999 |
| WO | 96/37156 A1 | 11/1996 |
| WO | 97/23169 A1 | 7/1997 |

* cited by examiner

*Primary Examiner* — Joseph A Stoklosa
*Assistant Examiner* — Marina Delaney Templeton
(74) *Attorney, Agent, or Firm* — Oliff PLC

(57) ABSTRACT

An electrode instrument and a resectoscope, wherein a cross section of the at least one electrode carrier is locally enlarged between the distal end of the electrode carrier and a guide element.

10 Claims, 1 Drawing Sheet

RESECTOSCOPE AND ELECTRODE INSTRUMENT FOR A RESECTOSCOPE

The invention relates to an electrode instrument for a resectoscope. The invention furthermore relates to a resectoscope.

Surgical radiofrequency instruments, for example resectoscopes, are used to remove or manipulate body tissue. Typical applications are those in urology. Prostate resection is an example thereof. A radiofrequency tool employed may be an electrode, that is to say an RF electrode, which is connected to a radiofrequency generator, an operator being able to activate and deactivate the generator using a switch. The radiofrequency current causes a plasma to be formed at the electrode. Because of the interaction of the plasma with the tissue, RF electrodes are particularly suitable for highly accurate manipulation of the tissue.

In order to manipulate the tissue, depending on the application, the electrode may be configured as a cutting loop or as a button electrode, or alternatively as a needle, roller, band, etc., which when the radiofrequency voltage is turned on, because of the plasma, can be guided very easily and with almost no resistance through the body tissue to be removed.

The electrode is secured releasably by an electrode instrument to a transporter, that is to say a working element of the resectoscope. During the treatment of the body tissue, the electrode instrument is moved with the electrode along a longitudinal direction of the resectoscope. Depending on whether the resectoscope is an active or passive resectoscope, the transporter, or the carriage, is connected by a compression spring or a tension spring to a main body that has a gripping unit.

Known electrode instruments are guided together with optics, which may be configured as a light guide or a rod lens system in a tubular shaft of the resectoscope. This shaft extends from the proximal end to the distal end of the resectoscope and, for the treatment, is guided into the body to be treated. The electrode instrument is in this case coupled movably with the optics or with an inner shaft, in which the optics are located. This may for example be done by means of a guide tube or a metal guide plate, which at least partially encloses the optics or the inner shaft. The metal guide plates in this case locally connect the two electrode carriers, which are configured substantially parallel. In known exemplary embodiments, the electrode carriers are assigned a distal and a proximal metal guide plate and optionally further metal guide plates, the distal metal guide plate being assigned to a distal region and the proximal metal guide plate being assigned to a proximal region on the electrode carriers.

So that the electrode, to which an RF current can be applied, does not accidentally come in contact with the metal inner shaft, the inner shaft has an instrument tip made of plastic. This instrument tip is assigned to a distal end of the inner shaft. The distal end of the electrode carrier, together with the electrode, extends through this sleeve-like instrument tip, the electrode together with the electrode carriers being movable to and from during the operation relative to the instrument tip along a longitudinal axis. The instrument tip is mounted freely movably on the distal segments of the two electrode carriers. For this purpose, the two electrode carriers are guided through recesses or bores of the instrument tip.

In order to couple the electrode carriers with the inner shaft, the latter is fitted onto or under the two U-shaped metal guide plates, or the electrode carriers are fitted with the metal guide plates onto or under the inner shaft. When the inner shaft is fitted or clipped onto the metal guide plates, the latter are elastically deformed. During assembly of the electrode instrument with the inner shaft, it may occur that the instrument tip freely movable on the electrode carriers slips in the proximal direction onto a metal guide plate, in particular onto a distal metal guide plate. When the metal guide plates are then elastically bent in order to receive the inner shaft, this force is also transmitted via the electrode carriers onto the instrument tip. The force which may then act on the instrument tip made of plastic because of the electrode carriers is sufficient to deform the instrument tip plastically, that is to say irreversibly. This deformation of the instrument tip may lead to the electrode instrument becoming unusable, since the instrument tip can no longer be slid freely over the electrode carriers.

The object of the invention is to provide an electrode instrument and a resectoscope, by which the aforementioned problem is solved.

A solution to this object is described by the features of claim 1. Accordingly it is provided that a cross section of at least one electrode carrier is locally enlarged between the distal end of the electrode carrier and a guide element, which may for example be a metal guide plate. Furthermore, according to the invention an instrument tip is arranged on a distal segment of the electrode carriers. The cross-sectional enlargement of the at least one electrode carrier is arranged in front of the instrument tip as seen in the proximal direction. According to another exemplary embodiment, the cross section of at least one electrode carrier may be enlarged between the instrument tip and the at least one guide element, preferably a distal guide element. This cross-sectional enlargement on at least one electrode carrier prevents the instrument tip from slipping into the vicinity of or directly in front of the guide element. The force described above, which acts on the instrument tip during the elastic deformation of the guide elements, is commensurately smaller when the distance between the instrument tip and the guide element, in particular the distal guide element, is greater. By virtue of the cross-sectional enlargement, it is possible to provide a sufficiently large distance between the instrument tip and the guide element. The distance between the cross-sectional enlargement and the electrode is in this case still sufficiently large for the electrode to be moved to and fro along the shaft axis during the operation.

According to one preferred exemplary embodiment, the cross-sectional enlargement of the at least one electrode carrier may have an oval shape, the cross-sectional enlargement having an oval shape in relation to a cross section of the electrode carrier. Preferably, this oval shape is aligned perpendicularly to a plane defined by the two electrode carriers. By this shape and the alignment of the cross-sectional enlargement, it is possible to ensure that the electrode carriers can move freely to and fro relative to the inner shaft, and in particular also relative to an outer shaft. The functionality or the mobility of the electrode instrument relative to the inner shaft is therefore not affected by the cross-sectional enlargement. It is also conceivable for the cross-sectional enlargement to have a different shape, for example a sickle shape, the sickle then being adapted to the shape of the inner shaft.

In particular, according to the invention the cross-sectional enlargement of the at least one electrode carrier consists in crimping a sleeve to the electrode carrier, applying a solder spot on the electrode carriers, or the like, or deforming or reshaping the electrode carrier. It is also conceivable for a pin, a web or a different kind of projection, with which the cross section can be enlarged, to be arranged on the at least one electrode carrier. Because of this cross-sectional enlargement, the instrument tip can be displaced only limitedly on the electrode carriers. Thus, a movement of the instrument tip into a critical vicinity of the guide element is prevented. The instrument tip therefore never enters the region in which it can be plastically deformed by the elastic bending of the guide element.

It is conceivable for the instrument tip to have two bores, through which the two electrode carriers are guided, the instrument tip being mounted freely movably on the two electrode carriers. The cross-sectional enlargement is then dimensioned precisely in such a way that it is larger than at least one bore through the instrument tip. During planned or unplanned movement of the instrument tip to and fro on the electrode carriers, the instrument tip therefore abuts against the enlargement and therefore reaches a minimum distance from the guide element. The force action during the bending of the at least one guide element, which the instrument tip experiences at this minimum distance, is negligible, that is to say not detrimental to the shape of the instrument tip.

Furthermore, a preferred exemplary embodiment is provided in which both electrode carriers have a cross-sectional enlargement, the latter being dimensioned in such a way that the instrument tip cannot be displaced beyond the cross-sectional enlargements. The cross-sectional enlargements per se in this case are each smaller than a diameter of the bores. By mirror-image positioning of the cross-sectional enlargements, which may for example be pins, the instrument tip cannot however move beyond the cross-sectional enlargement. By deliberate bending or compression of the electrode carriers, it is however possible to align the cross-sectional enlargements in such a way that the instrument tip can be displaced in the proximal direction into the vicinity of the guide elements. This, however, is possible only as a result of manual intervention by an operator. Otherwise, as described above, the cross-sectional enlargements prevent the instrument tip from being able to enter the critical region in front of the guide element.

According to another exemplary embodiment, the instrument tip may be slid against a slight resistance onto the cross-sectional enlargements. The instrument tip is held there in its position, for example by increased friction or elastic deformation. After clipping of the electrode onto the inner shaft, it is slid in the proximal direction in order to secure it. The instrument tip is in this case coupled with the distal end of the inner shaft without further handling and is slid downward against the corresponding resistance of the cross-sectional enlargements, so that it is again movable relative to the electrode.

Preferably, it is conceivable for the distal guide element to be offset in relation to the distal end of the electrode carrier in the proximal direction by from 10 mm to 100 mm, in particular from 25 mm to 85 mm, preferably by 55 mm. It is furthermore conceivable for the cross-sectional enlargement to be at a distance of from 10 mm to 60 mm, preferably from 20 mm to 40 mm, or 30 mm, from the electrode. The distance between the cross-sectional enlargement and a distal end of the guide element, in particular of the distal guide element, is from 10 mm to 100 mm, preferably 45 mm.

Lastly, a further solution to the object mentioned in the introduction is described by a resectoscope. This resectoscope has an electrode instrument. The resectoscope furthermore has an inner shaft, in which optics are mounted, the electrode instrument being guidable on the inner shaft with at least one guide element, preferably a metal guide plate.

A preferred exemplary embodiment of the invention will be described below in more detail with the aid of the drawing, in which.

Figure 1:
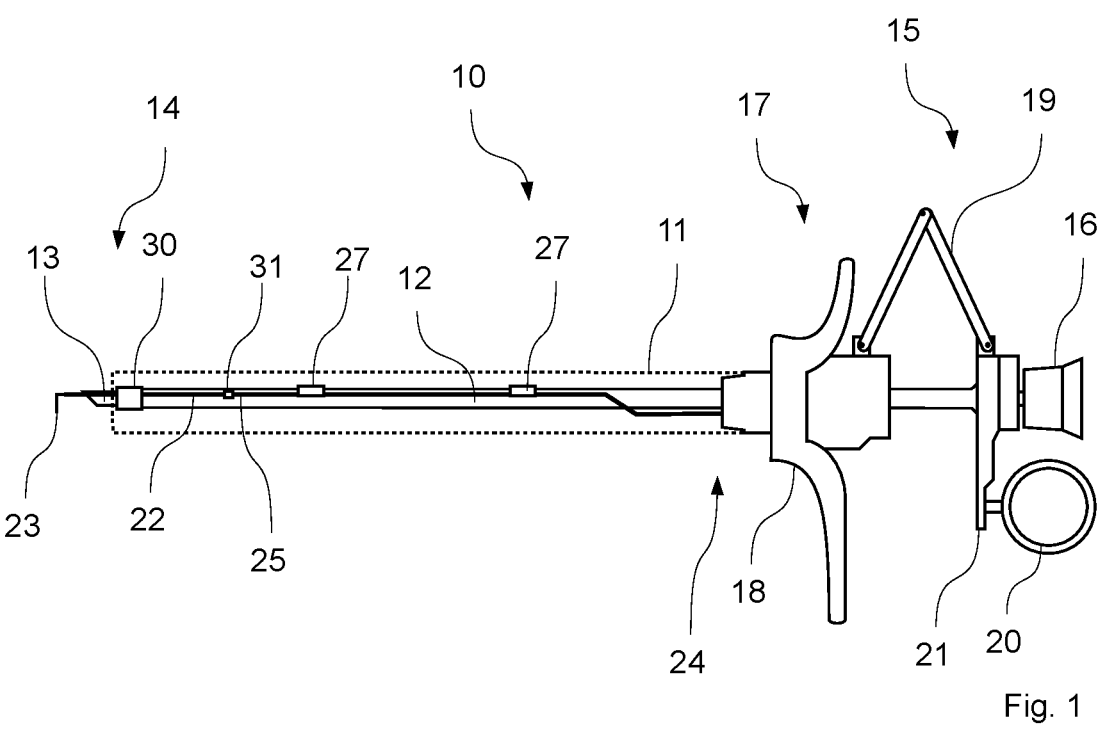
FIG. 1 shows a schematic representation of a resectoscope.

FIG. 1 represents a possible exemplary embodiment of a resectoscope 10. In this resectoscope 10, an outer shaft 11, indicated here only by dashed lines, is slid over an inner shaft 12. The inner shaft 12 is used to receive or guide optics 13, which extend from a distal end 14 to a proximal end 15 of the resectoscope 10. At the proximal end 15, a user is provided with an eyepiece 16 in order to observe the region to be operated on in front of the distal end 14 through the optics 13.

One essential component of the resectoscope 10 is the transporter 17. This transporter 17 has inter glia a first gripping means 18, and is connected by means of a spring element 19 to a second gripping means 20 and to an optics plate 21.

Figure 2:
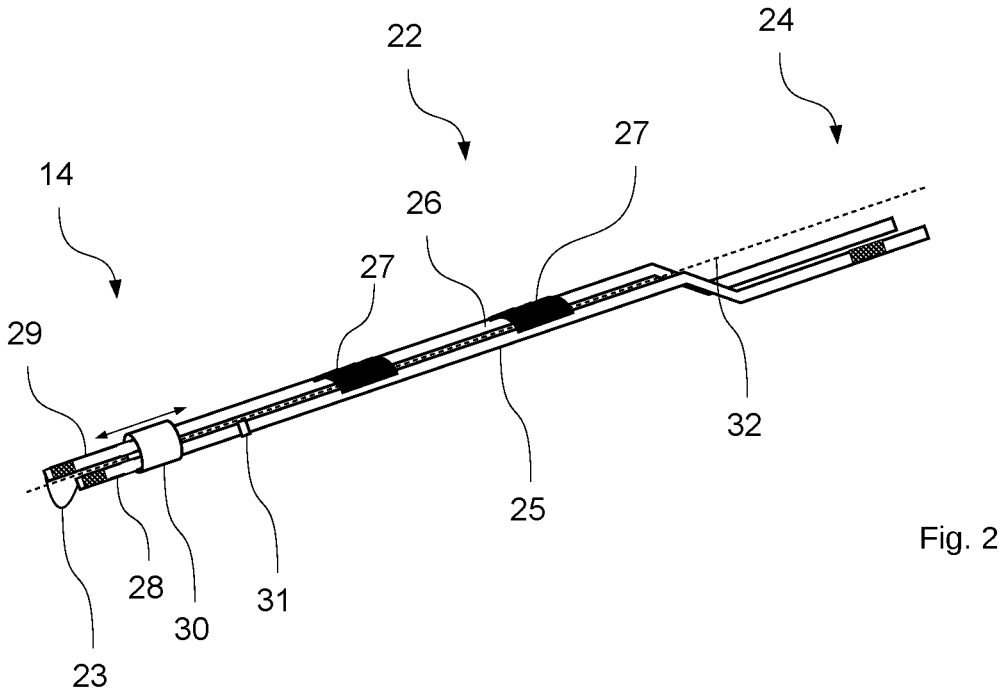
FIG. 2 shows a schematic perspective representation of an electrode instrument.

Furthermore, an electrode instrument 22 extends along the inner shaft 12 from the distal end 14 of the resectoscope 10 to the transporter 17. The electrode instrument 22 represented in FIG. 2 is only one possible exemplary embodiment. It should expressly be pointed out that the invention described here is not meant to be restricted to the form represented here. Rather, it is conceivable that the described invention may also be usable in connection with electrode instruments shaped in different ways.

The electrode instrument 22 represented here can be secured with a proximal end 24 in the transporter 17. In this way, the electrode instrument 22 can on the one hand straightforwardly be decoupled from the transporter 17, or coupled to the transporter 17, and on the other hand move together with the transporter 17 along the longitudinal axis of the resectoscope 10 in the distal or proximal direction.

At the distal end 14 of the electrode instrument 22, the latter has an electrode 23. This electrode 23, or cutting electrode, can be supplied by means of an RF generator (not represented) with electrical energy that is used to manipulate tissue. By the application of an RF voltage to the electrode, a plasma is formed around the electrode 23, represented here as a cutting loop. By an axial movement of the electrode instrument 22 forward and backward, the organic tissue can be manipulated, or cut, Besides the cutting loop represented in the figures, other electrode shapes may also be envisioned.

For the highly accurate manipulation of human tissue, it is extremely important that the electrode 23 can be handled very precisely. This precise handling is impeded in particular by the length of the electrode instrument 22, or by a reduction of the cross section of the instrument 22.

As may be seen in FIG. 2, the electrode 23 is mechanically fastened or fastenable with its ends on two electrode carriers 25 and 26, or on two electrode sleeve tubes or forked tubes. The electrode 23 together with the electrode carriers 25 and 26 represent the essential components of the electrode instrument 22. Besides the parallel guiding represented here of the electrode carriers 25 and 26, or of the electrode sleeve tubes, it is also conceivable for the electrode carriers 25 and 26 to be configured in a forked fashion and to converge in the direction of the proximal end 15 to form a shaft.

Besides the mechanical connection, the electrode carriers 25 and 26, or the electrode sleeve tubes, are also used for the electrical contacting of the electrode 23. It is provided that the electrode carriers 25 and 26 as well as electrical conductors inside the carriers 25 and 26 are used as electrical lines, or contacts.

In order to increase the stability and the associated secure or precise handling of the electrode instrument 22, according to the invention the electrode carriers 25, 26 are connected to one another by a guide element 27. Furthermore, it may be provided, or it is conceivable, that the two electrode carriers 25, 26 are connected to one another by at least one further guide element 27.

This guide element 27 is used not only to stabilize the electrode instrument 22 as a whole, but also for guiding along the inner shaft 12. The at least one guide element 27 is in this case placed or clamped, or clipped, onto a lateral face of the inner shaft 12, with the at least one guide element 27 enclosing the inner shaft 12 at least partially. As an alternative, it is also conceivable that the at least one guide element 27 may be fastened on the electrode carriers 25, 26 from below, the electrode instrument 22 then being located below a longitudinal axis 32 of the inner shaft 12.

During the damping or clipping of the inner shaft 12 onto the at least one guide element 27, the two electrode carriers 25, 26 are slightly bent so that the inner shaft 12 can be fitted with its outer contour between the electrode carriers 25, 26 and the guide element 27. In the clamped state of the inner shaft 12, the two electrode carriers 25, 26 return to their original parallel, or non-bent, shape. In this state, the electrode instrument 22 can move parallel to the longitudinal axis 32 against only a small friction resistance.

In order to insulate the electrode 23, to which an electrical potential is applied, electrically from the inner shaft 12, or to prevent the electrode 23 from coming in contact with the metal inner shaft 12 and electrical discharges being able to form between the electrode 23 and the inner shaft 12, the inner shaft 12 is assigned an instrument tip 30 made of plastic. This instrument tip 30 is assigned to the distal end 14 of the electrode instrument 22 during assembly. One possible exemplary embodiment of this is represented in a highly schematized way in FIG. 2. The instrument tip 30 has a central opening, which corresponds substantially with the inner diameter of the inner shaft 12. The instrument tip 30 furthermore has two bores, through which the segments 28 and 29 of the electrode carriers 25, 26 are guided. The instrument tip 30 can thus be displaced freely to and fro on the two electrode carriers 25, 26 along the longitudinal axis 32. After the above-described joining of the inner shaft 12 to the at least one guide element 27, the instrument tip 30 and the inner shaft 12 are displaced relative to one another along the longitudinal axis 32 so that they can be brought in contact. By a coupling mechanism, the instrument tip 30 can be coupled releasably with a distal end of the inner shaft 12. The instrument tip 30 together with the inner shaft 12 can therefore be displaced relative to the electrode instrument 22 along the longitudinal axis 32 in order to manipulate body tissue with the electrode 23, as described above.

As already described, the electrode carriers 25, 26 are bent slightly out of their parallel setting during the joining of the inner shaft 12 to the electrode instrument 22, or to the at least one guide element 27. Elastic bending of the guide element 27 also takes place in this case. So that this bending is not hindered by the instrument tip 30, or so that the force that is used for the bending is not transmitted onto the instrument tip 30 and plastically deforms it, the instrument tip 30 must be located at a sufficient distance on the electrode carriers 25, 26 from the guide element 27. So that the instrument tip 30 does not slip accidentally into the immediate vicinity of the guide element 27, according to the invention the cross section of at least one electrode carrier 25, 26 has an enlargement between the instrument tip 30 and the guide element 27. Because of this local or localized cross-sectional enlargement 31, the cross section of at least one electrode carrier 25, 26 is larger than one of the bores through the instrument tip 30. The instrument tip 30 can therefore no longer move freely on the electrode carriers 25, 26, or arbitrarily close to the guide element 27. Instead, the movement of the instrument tip 30 in the direction of the guide element 27 is prevented by the cross-sectional enlargement 31 (FIG. 2).

This cross-sectional enlargement 31 may, for example, consist in a crimping of the at least one electrode carrier 25, 26. A sleeve is in this case placed onto at least one electrode carrier 25, 26 and crimped. As an alternative, the shape of the at least one electrode carrier 26 may also be modified at this position in such a way that the cross section is larger than a bore of the instrument tip 30. It is also conceivable for both electrode carriers 25, 26 to have a corresponding cross-sectional enlargement 31. In order to prevent the instrument tip from being plastically deformed during the installation of the inner shaft 12, the at least one cross-sectional enlargement 31 must be arranged at a sufficient distance from the guide element 27. The distance may in this case be configured as a function of the shape and design of the electrode instrument 22. Conceivable distances may be from 10 mm to 100 mm, preferably from 20 mm to 60 mm, or 40 mm.

So that the cross-sectional enlargement 31 does not affect the relative movement between the electrode instrument 22 and the inner shaft 12, according to the invention the shape of the cross-sectional enlargement 31 is matched to the outer contour of the inner shaft 12. For example, the cross-sectional enlargement 31 may in this case assume an oval or sickle-like cross section. Likewise, the cross-sectional enlargement 31 is shaped, or dimensioned, in such a way that it also does not come in contact with the shaft 11.

LIST OF REFERENCES

10 resectoscope
11 shaft
12 inner shaft
13 optics
14 distal end
15 proximal end
16 eyepiece
17 transporter
18 first gripping means
19 spring element
20 second gripping means
21 optics plate
22 electrode instrument
23 electrode
24 proximal end
25 electrode carrier
26 electrode carrier
27 guide element
28 segment
29 segment
30 instrument tip
31 cross-sectional enlargement
32 longitudinal axis

The invention claimed is:

1. An electrode instrument for a resectoscope having an electrode, the electrode being fastened to two distal ends of two electrode carriers aligned parallel with one another, and at least one guide element that connects the two electrode carriers to one another being arranged on the electrode carriers, wherein:

a cross section of at least one of the two electrode carriers is locally enlarged between the two distal ends of the two electrode carriers and the at least one guide element;

an instrument tip is arranged on distal portions of the two electrode carriers and configured to move freely along the distal portions of the two electrode carriers; and the locally enlarged cross section of at least one of the two electrode carriers between the instrument tip and the at least one guide element is configured to prevent the instrument tip from moving within a predetermined distance of the guide element.

2. The electrode instrument for a resectoscope as claimed in claim 1, wherein the locally enlarged cross section is arranged in front of the instrument tip as seen in a proximal direction.

3. The electrode instrument for a resectoscope as claimed in claim 1, wherein the locally enlarged cross section has an oval shape, the cross-sectional enlargement having an oval shape in comparison to a cross section of one of the two electrode carriers.

4. The electrode instrument for a resectoscope as claimed in claim 3, wherein the oval shape is aligned perpendicularly to a plane defined by the two electrode carriers.

5. The electrode instrument for a resectoscope as claimed in claim 1, wherein crimping a sleeve to the two electrode carriers and applying a solder spot on the two electrode carriers forms the locally enlarged cross section of the at least one of the two electrode carriers.

6. The electrode instrument for a resectoscope as claimed in claim 1, wherein the instrument tip has two bores, through which the two electrode carriers are guided, the instrument tip being mounted such that the instrument tip is configured to move freely along the two electrode carriers.

7. The electrode instrument for a resectoscope as claimed in claim 6, wherein the locally enlarged cross section is larger than the bore through the instrument tip.

8. The electrode instrument for a resectoscope as claimed in claim 1, wherein the two electrode carriers have a cross-sectional enlargement, these being dimensioned in such a way that the instrument tip move beyond the cross-sectional enlargements.

9. The electrode instrument for a resectoscope as claimed in claim 1, wherein a distal guide element is offset in relation to the distal end of the electrode carrier in a proximal direction by from 10 mm to 100 mm.

10. A resectoscope having the electrode instrument as claimed in claim 1 and an inner shaft, in which optics are mounted, the electrode instrument being guidable with at least one guide element on the inner shaft.

* * * * *